(12) United States Patent
Gleiman et al.

(10) Patent No.: US 8,753,360 B2
(45) Date of Patent: Jun. 17, 2014

(54) EXPANDABLE MESH SYSTEM AND METHOD OF USE THEREFOR

(75) Inventors: Seth Gleiman, Branford, CT (US); Michael Prescott, Hamden, CT (US)

(73) Assignee: Covidien LP, Mansfield, MA (US)

( * ) Notice: Subject to any disclaimer, the term of this patent is extended or adjusted under 35 U.S.C. 154(b) by 369 days.

(21) Appl. No.: 12/941,273

(22) Filed: Nov. 8, 2010

(65) Prior Publication Data
US 2012/0116423 A1    May 10, 2012

(51) Int. Cl.
*A61F 2/00* (2006.01)
(52) U.S. Cl.
CPC ....... *A61F 2/0063* (2013.01); *A61F 2002/0072* (2013.01)
USPC .......................................................... 606/151
(58) Field of Classification Search
CPC ........... A61F 2/0063; A61F 2002/0068; A61F 2002/0072
USPC .............. 63/9, 38; 623/2.37, 23.72; 24/703.4, 24/703.5, 713; 606/151; 600/141–142, 37
See application file for complete search history.

(56) References Cited

U.S. PATENT DOCUMENTS

| | | | |
|---|---|---|---|
| 3,060,972 A | 10/1962 | Sheldon | |
| 3,625,200 A | 12/1971 | Muller | |
| 3,727,609 A | 4/1973 | Hale | |
| 3,855,598 A | 12/1974 | Keller | |
| 4,054,128 A | 10/1977 | Seufert et al. | |
| 4,679,392 A | 7/1987 | Nakagawa | |
| 5,077,988 A | 1/1992 | Pöll | |
| 5,370,475 A | 12/1994 | LeBlanc | |
| 5,629,077 A | 5/1997 | Turnlund et al. | |
| 5,766,176 A | 6/1998 | Duncan | |
| 5,916,225 A | 6/1999 | Kugel | |
| 5,961,554 A | 10/1999 | Janson et al. | |
| 6,176,863 B1 | 1/2001 | Kugel et al. | |
| 6,241,572 B1 | 6/2001 | Braginsky | |
| 6,378,334 B1 | 4/2002 | Hector | |
| 6,442,972 B1 | 9/2002 | Watson | |
| 6,463,759 B1 | 10/2002 | Garcia et al. | |
| 6,464,720 B2 | 10/2002 | Boatman et al. | |
| 6,477,861 B1 | 11/2002 | Pottick | |
| D475,094 S | 5/2003 | Ko | |
| 6,589,891 B1 | 7/2003 | Rast | |
| 6,740,028 B2 | 5/2004 | Boone et al. | |
| D494,737 S | 8/2004 | Schaefer | |
| 6,769,270 B2 | 8/2004 | Takessian | |
| 6,908,065 B1 | 6/2005 | Ritchie | |
| 6,991,141 B2 | 1/2006 | Ciko et al. | |
| 7,040,120 B2 | 5/2006 | Hunter | |

(Continued)

FOREIGN PATENT DOCUMENTS

WO    WO 94/17747 A1    8/1994

OTHER PUBLICATIONS

European Search Report for EP 11250758.7-2320 date of completion is May 25, 2012 (7 pages).

*Primary Examiner* — Julian W Woo
*Assistant Examiner* — Shaun L David (57) ABSTRACT

A surgical mesh includes a patch, a plurality of nesting lugs or beads and a wire interconnecting the plurality of nesting lugs. The plurality of nesting lugs is associated with the patch such that the surgical mesh is movable between a flexible state when there is no tension in the wire and a substantially rigid state when tension is applied to the wire.

15 Claims, 12 Drawing Sheets

(56) References Cited

U.S. PATENT DOCUMENTS

| | | |
|---|---|---|
| 7,226,409 B2 | 6/2007 | Peng et al. |
| 7,252,681 B2 | 8/2007 | Berg et al. |
| 7,322,214 B2 | 1/2008 | Ignatowski |
| 7,328,528 B2 | 2/2008 | Caminiti |
| D563,493 S | 3/2008 | Nelson et al. |
| 7,406,840 B2 | 8/2008 | Brancato |
| 7,444,801 B2 | 11/2008 | Rosenwasser et al. |
| 7,462,190 B2 | 12/2008 | Lombardi |
| 7,640,617 B2 * | 1/2010 | Kennedy et al. ............ 15/144.1 |
| 2002/0173804 A1 * | 11/2002 | Rousseau .................... 606/151 |
| 2003/0004581 A1 | 1/2003 | Rousseau |
| 2003/0205306 A1 | 11/2003 | Steinke |
| 2004/0134229 A1 | 7/2004 | Oliver |
| 2004/0172122 A1 | 9/2004 | Voinov |
| 2005/0090893 A1 | 4/2005 | Kavteladze et al. |
| 2005/0137514 A1 | 6/2005 | Vito et al. |
| 2006/0004252 A1 | 1/2006 | Astala |
| 2006/0094931 A1 * | 5/2006 | Danitz et al. ................ 600/141 |
| 2007/0156185 A1 | 7/2007 | Swanson et al. |
| 2007/0276308 A1 | 11/2007 | Huey et al. |
| 2007/0282443 A1 | 12/2007 | Globerman et al. |
| 2008/0033457 A1 | 2/2008 | Francischelli et al. |
| 2008/0086115 A1 | 4/2008 | Stoklund et al. |
| 2008/0109073 A1 | 5/2008 | Lashinski et al. |
| 2008/0132922 A1 | 6/2008 | Buevich et al. |
| 2008/0200980 A1 | 8/2008 | Robin et al. |
| 2008/0208329 A1 | 8/2008 | Bishop et al. |
| 2009/0024163 A1 | 1/2009 | Zeiner et al. |
| 2009/0065299 A1 | 3/2009 | Vito et al. |
| 2009/0082857 A1 | 3/2009 | Lashinski et al. |
| 2009/0088836 A1 | 4/2009 | Bishop et al. |
| 2009/0143777 A1 | 6/2009 | Pacey et al. |
| 2009/0156980 A1 | 6/2009 | Eaton et al. |
| 2009/0216245 A1 | 8/2009 | Viola |
| 2009/0227945 A1 | 9/2009 | Eaton et al. |
| 2009/0229608 A1 | 9/2009 | Eason et al. |
| 2009/0287293 A1 | 11/2009 | Mailhot, Jr. |
| 2009/0287307 A1 | 11/2009 | Parry et al. |

* cited by examiner

EXPANDABLE MESH SYSTEM AND METHOD OF USE THEREFOR

BACKGROUND

1. Technical Field

The present disclosure relates to a surgical mesh and, more particularly, to an expandable mesh system and a method of use therefore.

2. Background of Related Art

Surgical mesh of various types has long been known and used in surgical procedures. Much of the prior art surgical mesh was designed for use in conventional surgery from exterior of the body where a large enough incision is made to provide ample access for the insertion of a patch of surgical mesh in a desired position or orientation in the body where reconstruction or repair is required. However, when employed with laparoscopic surgical procedures, difficulties are often encountered in the insertion of conventional surgical mesh inside the body cavity through tubular trocars and in the subsequent positioning of the mesh in a desired orientation where reconstruction or repair is needed.

In minimally invasive procedures, a sheet of mesh is folded or rolled for introduction through one of the trocar access sheaths. Once wetted by bodily fluids at the repair site, the mesh may be difficult to spread smoothly over the repair site. The problem of positioning the mesh over the repair site is compounded when the mesh is placed between layers of tissue.

Specialized surgical devices have been developed to facilitate the use of conventional surgical mesh in laparoscopic surgery. In addition, various mechanisms have been proposed to facilitate the intraoperative expansion of surgical meshes to their flat shape or state, such as, for example, attaching a semi-rigid member to the surgical mesh. However, it is still difficult and time consuming to insert a patch of surgical mesh into a body cavity and positioning the inserted mesh using laparoscopic instruments against an internal defect where it is to be sutured.

SUMMARY

A surgical mesh implanted in the body either through an open incision or through a trocar associated with a laparoscopic procedure can be made to unfurl, expand and become flat for ease of positioning and fixation.

In accordance with one aspect of the present disclosure, a surgical mesh includes a patch, a plurality of nesting lugs and a wire interconnecting the plurality of nesting lugs. The plurality of nesting lugs is associated with the patch such that the surgical mesh is movable between a flexible state when there is no tension in the wire and a substantially rigid state when tension is applied to the wire.

In an embodiment, each of the plurality of nesting lugs may include a body portion and a neck portion extending from the body portion. The body portion may define a through hole dimensioned to receive the neck portion of an adjacent lug. The body portion may further define a recess dimensioned to at least partially receive the neck portion of the adjacent lug. The neck portion may be longitudinally tapered. The recess and the through hole may receive the neck portion of the adjacent lug when the surgical mesh is in a substantially rigid state. The neck portion may define a bore receiving therethrough the wire. The bore may be in communication with the through hole. The bore may have a diameter smaller than that of the wire. The surgical mesh may further include an end stop disposed adjacent a distal end of the wire. The distal end of the wire may include a knot.

In still another embodiment, each of the plurality of lugs may have a conical shape and may define a longitudinal bore therethrough. The plurality of lugs may partially overlap each other in respective longitudinal bores in a flexible state. At least one of the plurality of lugs may include a bend portion. The plurality of lugs may be biodegradable and bioabsorbable.

In still yet another embodiment, a surgical mesh includes a patch, a plurality of beads, and a wire interconnecting the plurality of beads. The plurality of beads is associated with the patch such that the surgical mesh is movable between a flexible state when there is no tension in the wire and a substantially rigid state when tension is applied to the wire.

In accordance with another aspect of the present disclosure, a method of expanding a surgical mesh adjacent a target surgical site includes providing a surgical mesh including a patch, a plurality of nesting lugs and a wire interconnecting the plurality of nesting lugs, applying tension to the wire, positioning the surgical mesh against the target surgical site and removing tension in the wire. The plurality of nesting lugs are associated with the patch such that the surgical mesh is movable between a flexible state when there is no tension in the wire and a substantially rigid state when tension is applied to the wire.

In an embodiment, the method may further include applying holding force to at least one of the plurality of lugs prior to applying tension to the wire. The step of applying tension to the wire may include applying a pushing force to a lug distal of the at least one of the plurality of lugs.

In another embodiment, the method may further include removing at least one of the plurality of lugs or the wire from the target surgical site.

In still another embodiment, a method of expanding a surgical mesh adjacent a target surgical site includes providing a surgical mesh including a patch, a plurality of beads and a wire interconnecting the plurality of beads, applying tension to the wire, positioning the surgical mesh against the target surgical site and removing tension in the wire. The plurality of beads are associated with the patch such that the surgical mesh is movable between a flexible state when there is no tension in the wire and a substantially rigid state when tension is applied to the wire.

BRIEF DESCRIPTION OF THE DRAWINGS

The above and other objects and features of the present disclosure will become apparent from the following description of embodiments given in conjunction with the accompanying drawings, in which.

DETAILED DESCRIPTION

Various embodiments of the presently disclosed surgical mesh system will now be described in detail with reference to the drawings, wherein like reference numerals identify similar or identical elements. In the drawings and in the description that follows, the term "proximal," will refer to the end of a device or system that is closer to the operator, while the term "distal" will refer to the end of the device or system that is farther from the operator.

Figure 1:
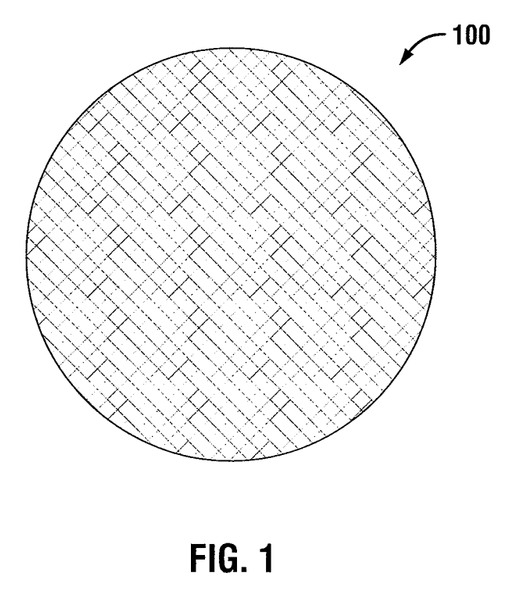
FIG. 1 is a top view of a surgical mesh system in accordance with an embodiment of the present disclosure.
Figure 2:
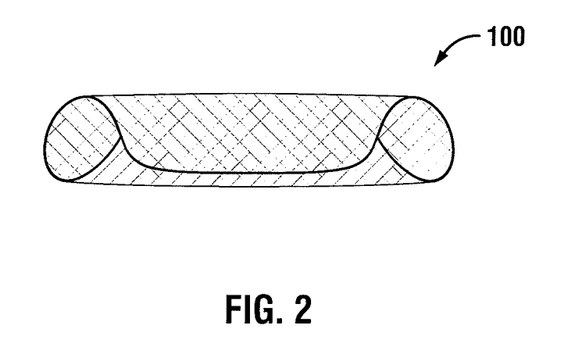
FIG. 2 is a perspective view of the surgical mesh system of FIG. 1 in a flexible state.

Referring now to FIGS. 1 and 2, an embodiment of the present disclosure is shown generally as a flexible mesh 100. Mesh 100 may be implanted in the body either through an open incision or through a trocar (i.e., access device) associated with a laparoscopic procedure. Mesh 100 may be made to unfurl, expand and to become flat for ease of positioning and fixation. In particular, mesh 100 is flexible such that mesh 100 has a generally collapsed shape (shown in FIG. 2) when it is in a first state and a generally expanded or flat shape when it is in a second state (as shown in FIG. 1).

Figure 3:
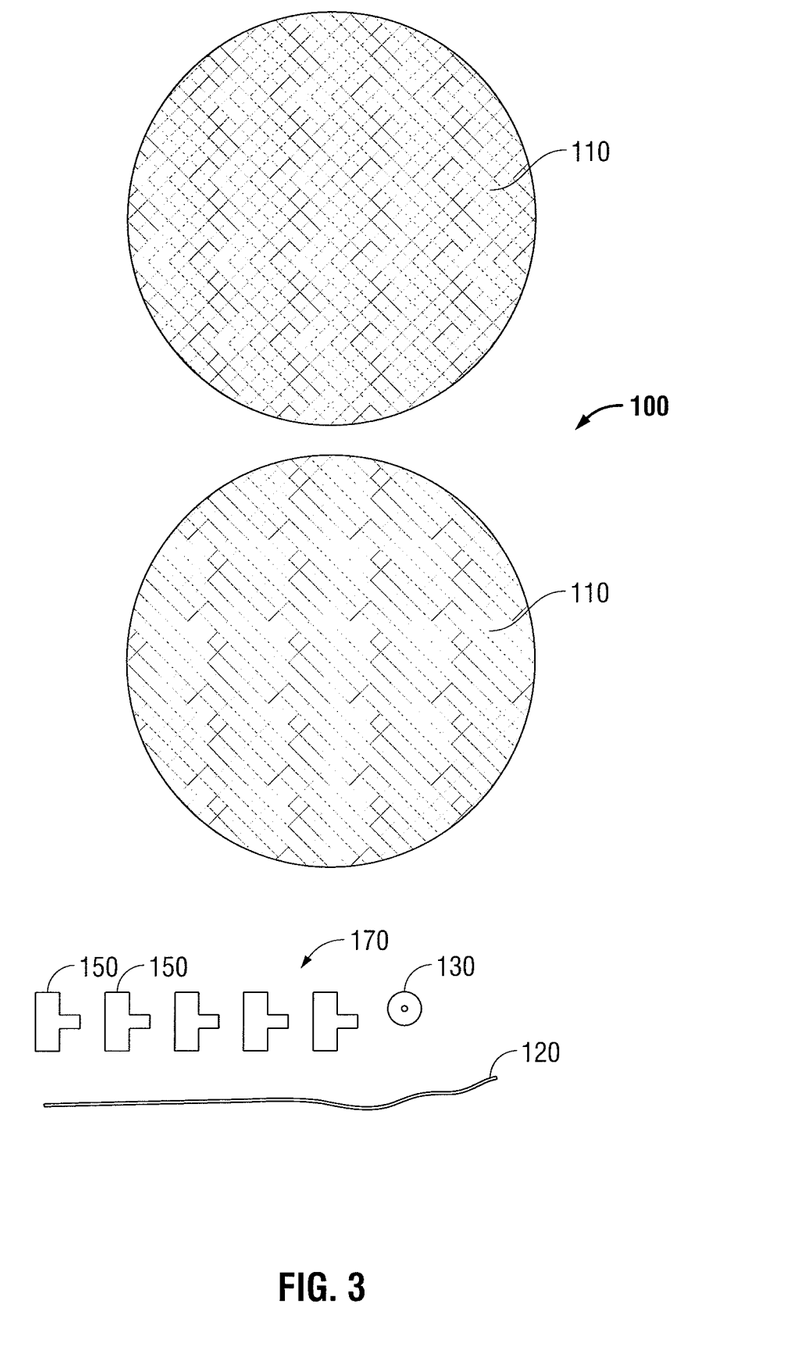
FIG. 3 is a top view the surgical mesh system of FIG. 1 with parts separated.

With reference to FIG. 3, mesh 100 includes a pair of patches 110, a plurality of nesting lugs 150, a wire 120 and an end stop 130. The pair of patches 110 may be fabricated of a mono-filament thread which is woven, knitted or otherwise formed into a fabric which is then cut to a desired shape. The threads from which the patch is fabricated are of a surgically clean material which is durable, flexible, essentially inextensible and resistant to corrosion from bodily fluids. The nesting lugs 150 are interconnected by wire 120 creating a strand 170 of lugs 150. Strand 170 is embedded or woven intermittently in the pair of patches 110 enabling the user to control the shape or the state of mesh 100 by controlling the tension in wire 120. For example, with little or no tension in wire 120, mesh 100 is in the flexible or first state (see FIG. 4). Upon applying tension to wire 120, lugs 150 nest, causing strand 170 to become rigid. The term "nest" is used herein to mean that a portion of a lug or a bead securely engages an adjacent lug or a bead. In this manner, mesh 100 expands to the second state without deforming from its intended shape. The flexibility of strand 170 may be varied by inclusion of more or less wire 120 for a given number of lugs 150. While a single continuous strand 170 may cover the entire mesh 100, a plurality of strands 170 may be utilized to accommodate, for example, special mesh shapes. However, in the interest of brevity, a single strand 170 will be illustrated throughout the application.

Figure 4:
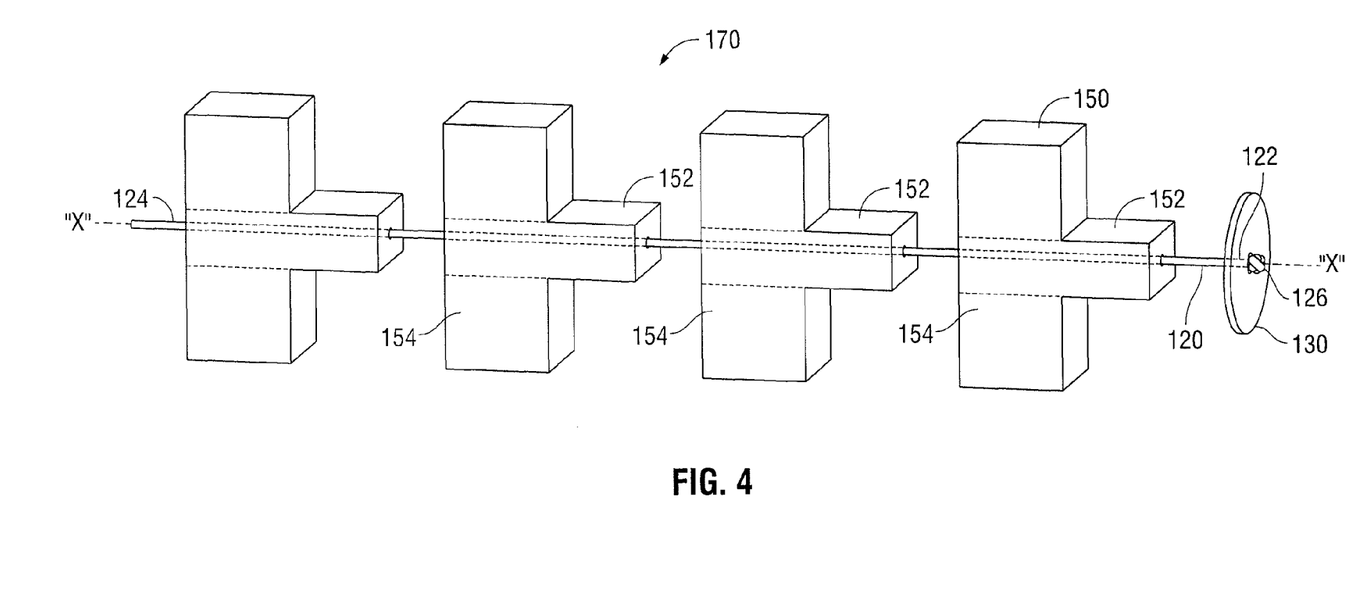
FIG. 4 is a perspective view of a strand of lugs for use with the surgical mesh system of FIG. 1.
Figure 5:
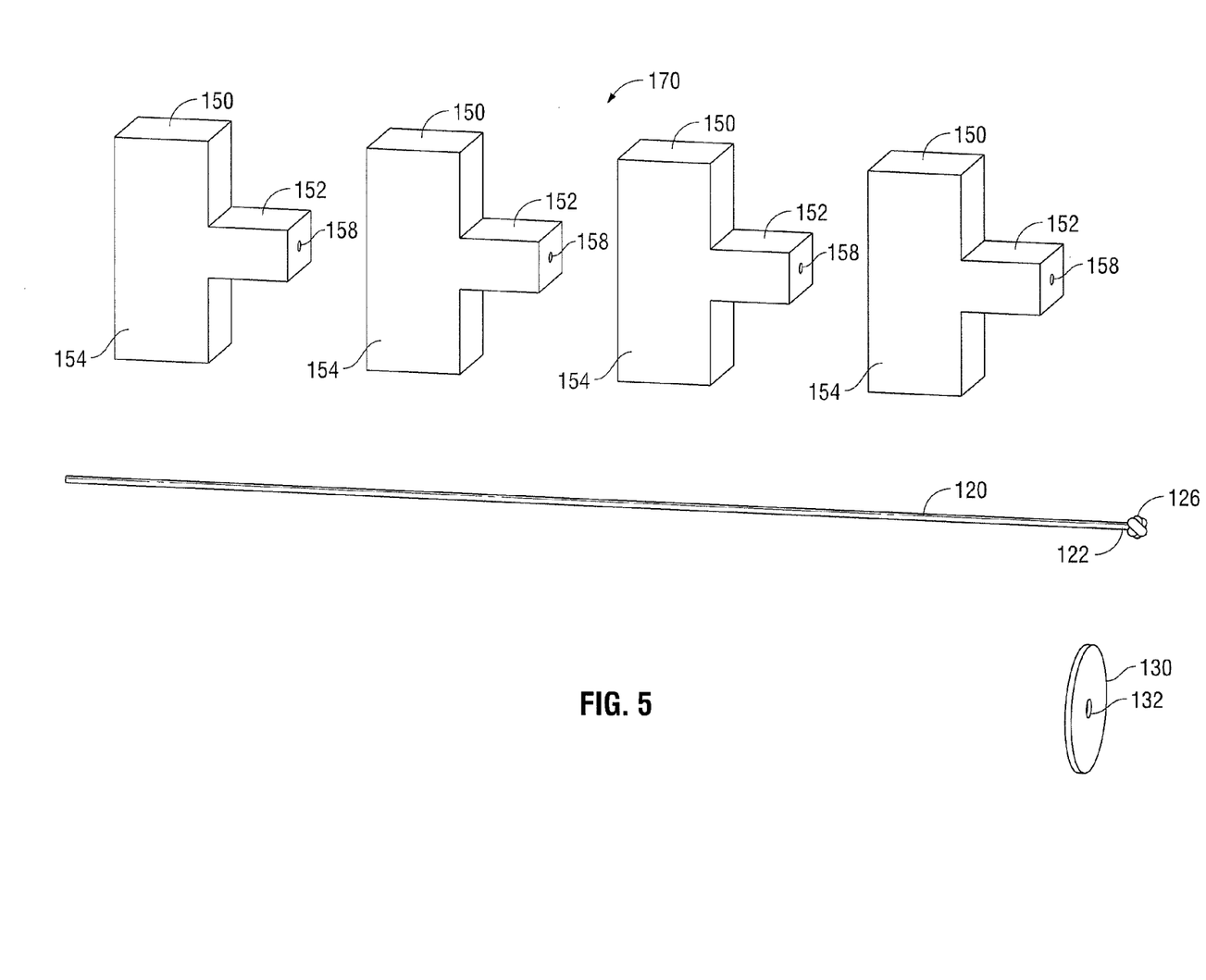
FIG. 5 is a perspective view of the strand of lugs of FIG. 4 with parts separated.
Figure 6:
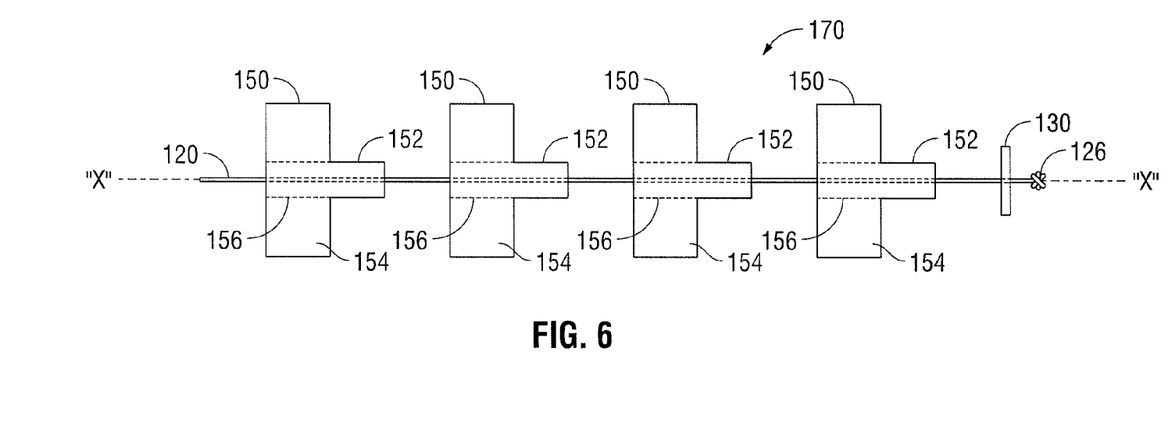
FIG. 6 is a side cross-sectional view of the strand of lugs of FIG. 4.

With reference now to FIGS. 4-6, a plurality of lugs 150 is arranged on wire 120. A distal end 122 of wire 120 may be securely fixed to a predetermined location on mesh 100 depending on the desired shape of mesh 100. End stop 130 is provided on wire 120, distal of the distal-most lug 150. End stop 130 may include a bore 132 through which wire 120 passes. Distal end 122 of wire 120 has a knot 126 which includes a diameter greater than that of bore 132 to prevent passage through bore 132. End stop 130 may be used to reduce concentration of the tensile force applied to mesh 100 when tension is applied to wire 120.

Figure 8A:
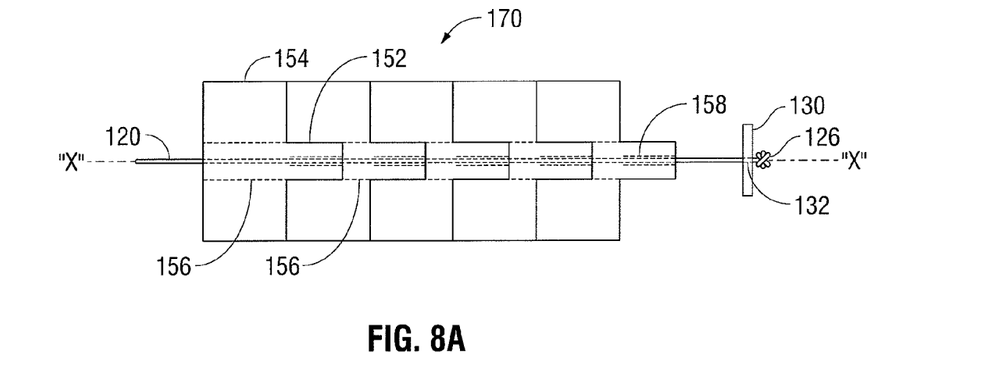
FIG. 8A is a side cross-sectional view of the strand of lugs of FIG. 4 in a rigid state.

Lug 150 includes a body portion 154 and a neck portion 152 extending from body portion 154. Neck portion 152 may be integrally formed with body portion 154. Body portion 154 defines a longitudinally extending through hole 156, as shown in phantom in FIG. 6. Through hole 156 is dimensioned to receive at least a portion of neck portion 152 of an adjacent lug 150 when lugs 150 are nested in the second state, as best shown in FIG. 8A. Neck portion defines a bore 158 in alignment with a longitudinal axis "X-X" defined by through hole 156. When lugs 150 are nested in the second state, neck portion 152 partially extends along a length of body 154 of an adjacent lug 150, as best shown in FIG. 8A. However, it is also contemplated that the length of neck portion 152 may be substantially equal to that of body portion 154, such that neck portion 152 may extend along the entire length of body portion 154 of the adjacent lug 150. Increasing the amount of neck portion 152 received in through hole 156 of body portion 154 may better secure the nested lugs 150 in the second position during surgical procedures which may require bending of strand 170. In both instances, the outside surfaces of nested lugs 150 are smooth with little deviation of the surface except for the seam between adjacent lugs 150.

Longitudinal bore 158 defined in neck portion 152 receives wire 120 therethrough. Bore 158 of neck portion 152 may be of a size smaller than the diameter of wire 120, for example, to frictionally hold wire 120 in place after it has been threaded through bore 158. In addition, wire 120 may include a pair of knots (not shown) for each lug 150. The pair of knots may be sized bigger than the diameter of bore 158. The first knot is formed distal of neck portion 152, and the second knot is formed proximal of neck portion 152. The predetermined placement of the pair of knots determines the allowed range of travel for each lug 150 on wire 120 between the first and second states. Thus, the pair of knots further enables uniform spacing of lugs 150 in mesh 100.

The placement of the pair of knots may determine the amount of neck portion 152 received in through hole 156 of body portion 154. For example, neck portion 152 having a length equal to that of body portion 152 may be partially received in through hole 156. In this manner, the rigidity of mesh 100 in the second state may be tailored to the application and reduction in number of lugs 150 used in mesh 100 may be achieved.

It is also contemplated that in order to facilitate the nesting of lugs 150 from the first state to the second state, the pair of knots may be formed on wire 120 such that neck portion 152 partially engages through hole 156 of body portion 154 of the adjacent lug 150 when strand 170 is in the first state. Thus, neck portion 152 remains in through hole 156 and engages in reciprocating movement within through hole 156 to and from a proximal portion of through hole 156 between the first and second states.

Figures 7A, 7B:
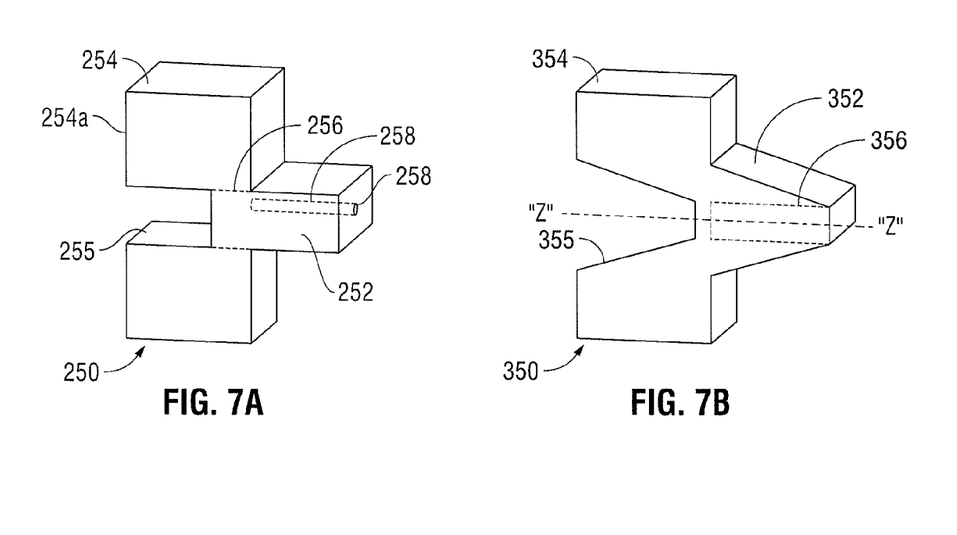
FIG. 7A is a perspective view of a lug in accordance with another embodiment of the present disclosure.
FIG. 7B is a perspective view of a lug in accordance with still another embodiment of the present disclosure.

According to another embodiment of the present disclosure, a lug 250 is illustrated in FIG. 7A. Lug 250 includes a body portion 254 and a neck portion 252 extending from body portion 254. Neck portion 252 may be integrally formed with body portion 254. A proximal portion 254a of body portion 254 defines a recess 255. Recess 255 is dimensioned to receive neck portion 252 of an adjacent lug 250. In particular, the entire neck portion 252 of the adjacent lug 250 may be received in recess 255. However, in order to further secure nested lugs 250, body portion 254 may define a longitudinally extending through hole 256 distal of recess 255. Through hole 256 may be in communication with recess 255 and dimensioned to receive a portion of neck portion 252 of the adjacent lug 250 when a strand 270 is in the second state. In this manner, neck portion 252 is disposed in recess 255 and through hole 256 of body portion 254 of the adjacent lug 250 when in the second state. In addition, neck portion includes a bore 258.

Figure 8B:
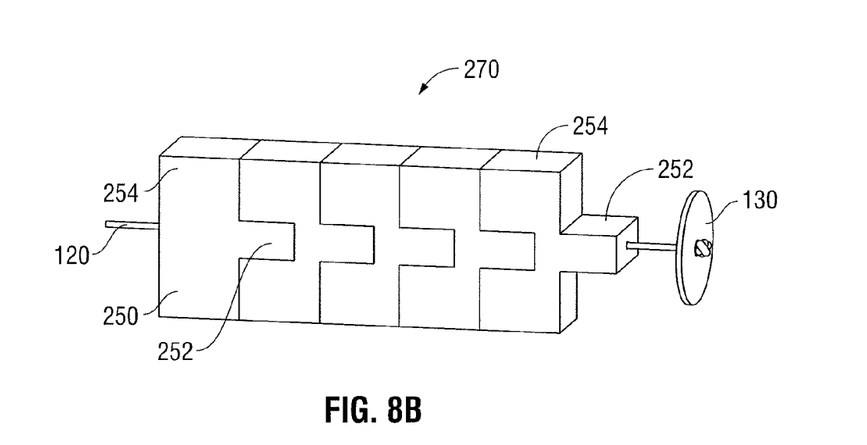
FIG. 8B is a perspective view of the strand of lugs of FIG. 7A in a rigid state.

With continued reference to FIG. 7A, when lugs 250 are nested in the second state, neck portion 252 partially extends along a length of body portion 254 of the adjacent lug 250, as best shown in FIG. 8B. However, it is also contemplated that the length of neck portion 254 may be equal to that of body portion 254, such that neck portion 252 may extend along the entire length of body portion 254 of the adjacent lug 250. Increasing the amount of neck portion 252 received in recess 255 and through hole 256 of body portion 254 may better secure the nested lugs 250 in the second state during surgical procedures which may require bending of strand 270.

The diameter of bore 258 may be smaller than that of wire 120, for example, to frictionally hold wire 120 in place after it has been threaded through bore 258. In addition, wire 120 may include a pair of knots (not shown) for each lug 250. The pair of knots may be sized bigger than the diameter of bore 258. The first knot is formed on wire 120 distal of neck portion 252 and the second knot is formed on wire 120 proximal of neck portion 252. The predetermined placement of the pair of knots determines the allowed range of travel for each lug 250 on wire 220 between the first and second states. Thus, the pair of knots further enables uniform spacing of lugs 250 in mesh 100.

According to still another embodiment of the present disclosure, a lug 350 is illustrated in FIG. 7B. Lug 350 is substantially similar to lug 250, and thus will only be described herein to the extent necessary to identify differences in construction and operation thereof. Throughout the following disclosure, like reference numeral will be used to identify like elements.

Neck portion 352 extends distally from a body portion 354 of a lug 350 defining a longitudinal axis "Z-Z". Neck portion 352 is tapered with respect to longitudinal axis "Z-Z." Body portion 354 defines a corresponding recess 355 longitudinally tapered with respect to longitudinal axis "Z-Z." Tapered neck portion 352 is dimensioned to be received in tapered recess 355 of an adjacent lug 350 when lugs 350 are nested in the second state. Moreover, when lugs 350 are nested in the second state, tapered neck portion 352 may be frictionally held in recess 355 of the adjacent lug 350. In addition, body portion 354 may further define a through hole 356 in communication with recess 355. The length of neck portion 352 may be substantially equal to that of body portion 354, such that neck portion 352 may extend along the entire length of body portion 354 of the adjacent lug 350. Increasing the amount of neck portion 352 received in recess 355 and through hole 356 of body portion 354 may better secure the nested lugs 350 in the second position during surgical procedures which may require bending of the strand. Wire 120 may be passed through through hole 356. However, it is further contemplated that neck portion 352 may define a longitudinal bore (not shown) for receiving therethrough wire 120. The bore may be of a size smaller than the diameter of wire 120, for example, to frictionally hold wire 120 in place after it has been threaded through the bore.

Neck portions 152, 252, 352 described herein include a non-circular cross-section. The non-circular cross-section may prevent rotation of a lug about the longitudinal axis when nested with an adjacent lug. However, it is further contemplated that a neck portion may have a circular cross-section to facilitate alignment of the neck portion with a through hole defined in a body portion.

With reference now to FIGS. 9A-9E, it is further envisioned that a lug may include various shapes and configurations. Each lug 550, 650, 750, 850, 950 defines a central bore 560, 660, 760, 860, 960 (shown in phantom) or a recess 955 dimensioned to receive a distal portion of an adjacent lug, as well as wire 120. In this manner, a strand of lugs 550, 650, 750, 850, 950 may become rigid and place the mesh in the second state.

Figure 9A:
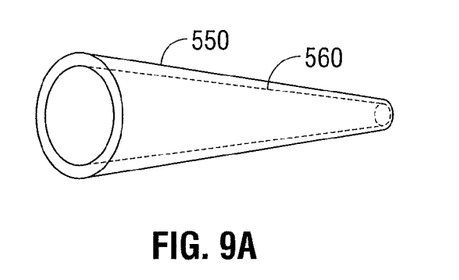
FIG. 9A-9E are perspective views of various alternate lugs for use with the surgical mesh system of FIG. 1.
Figure 9B:
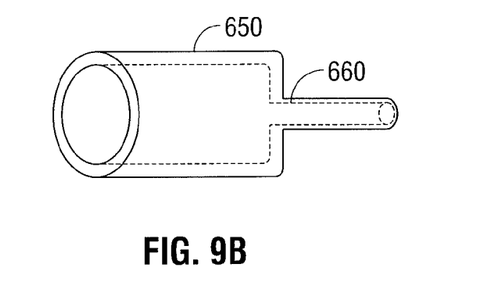
Figure 10:
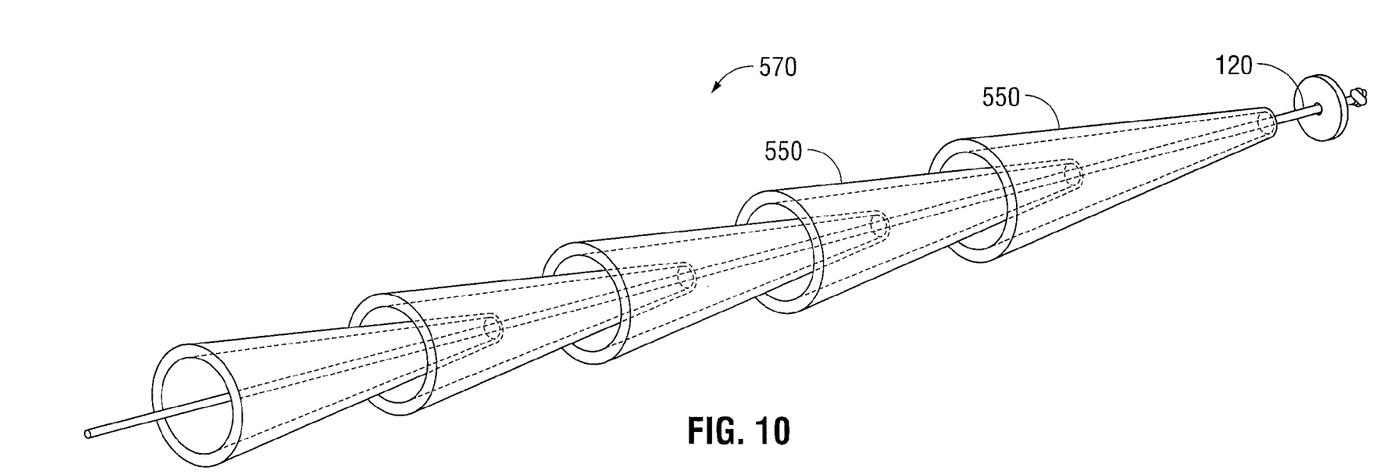
FIG. 10 is a perspective view of a strand of lugs of FIG. 9A in a flexible state.
Figure 11:
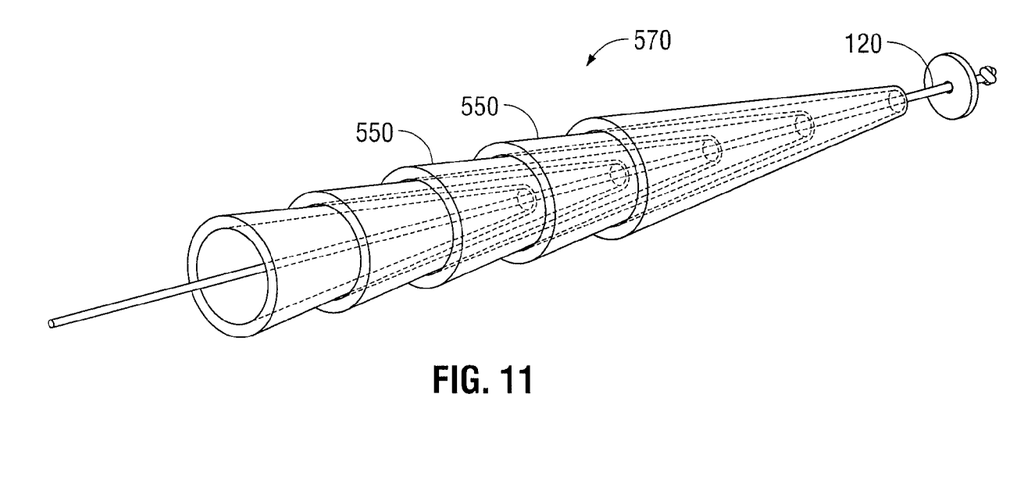
FIG. 11 is a perspective view of the strand of lugs of FIG. 9A in a rigid state.

With particular reference to FIG. 9A, lug 550 includes a conical shaped body, and defines central bore 560 for receiving adjacent lug 550 and wire 120 therein. As described with lug 150, a strand 570 of lugs 550 in the first state, as shown in FIG. 10, may become rigid, as shown in FIG. 11, for example, by application of tensile force to wire 120. In order to facilitate nesting of lugs 550 from the first state, a portion of lug 550 may be partially disposed within central bore 560 when strand 570 is in the first state.

Figure 9C:
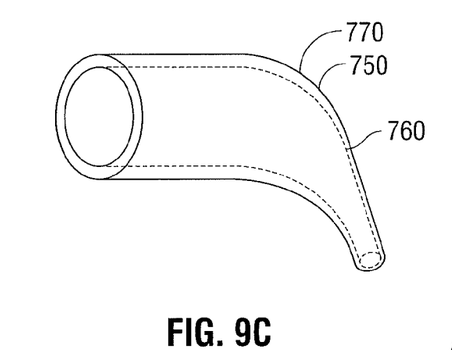
Figure 9D:
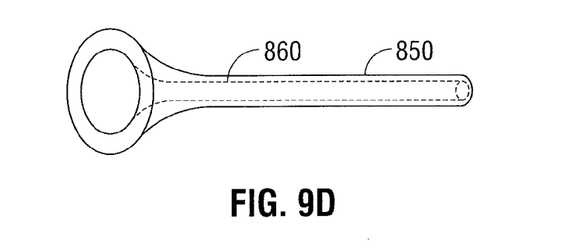
Figure 9E:
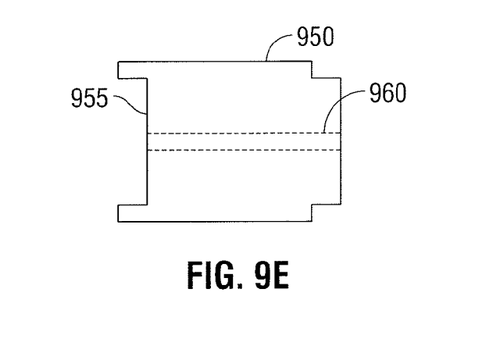

With particular reference now to FIG. 9C, lug 750 includes a bend portion 770 which may be used to accommodate special mesh shapes and redirection of the strand, that is, to redirect the tension force in wire 120 to another prescribed direction.

It is contemplated that lugs 150, 250, 350, 550, 650, 750, 850, 950 and wire 120 may be made from biodegradable and bioabsorbable materials. However, it is also contemplated that at least one of lugs 150, 250, 350, 550, 650, 750, 850, 950 or wire 120 may be made from a combination of non-biodegradable and non-bioabsorbable materials.

Figure 18A:
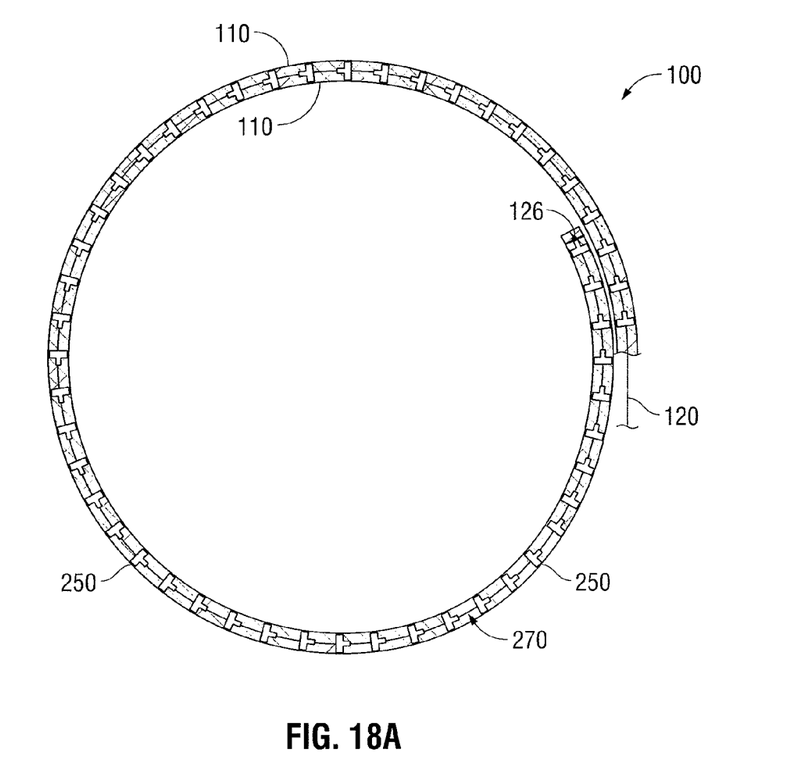
FIG. 18A is a cross-sectional view of a surgical mesh system including a strand of lugs of FIG. 7A in a flexible state.
Figure 18B:
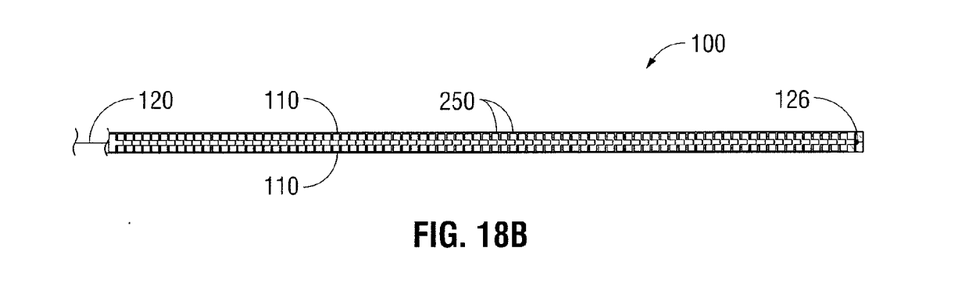
FIG. 18B is a cross-sectional view of the surgical mesh system of FIG. 18A in a in a rigid state.

With reference now to FIGS. 18A and 18B, a method of operation of mesh 100 will now be described. Mesh 100 may be implanted in the body either through an open incision or through a trocar associated with a laparoscopic procedure. First, flexible mesh 100 is placed in a flexible or folded state, as shown in FIG. 18A. Then mesh 100 may be positioned adjacent a target surgical site. Thereafter, mesh 100 may be made to become rigid and flat for ease of positioning and fixation, as shown in FIG. 18B. Mesh 100 may become rigid and flat upon application of a holding force to at least one of lugs 250, for example, lug 250 adjacent a proximal-most lug 250, and a tension force to wire 120. Alternatively, mesh 100 may become rigid and flat upon application of the holding force to, for example, a proximal-most lug 250, and a pushing force to, for example, lug 250 adjacent the proximal-most lug 250. Once mesh 100 is positioned at the desired location, tension in wire 120 is removed and strand 270 is returned to its flexible state so as to reduce patient discomfort. At this time, lugs 250 and wire 120 made from biodegradable and bioabsorbable materials may remain in or removed from the body. At least one of lugs 250 or wire 120 made from non-biodegradable and non-bioabsorbable materials may remain or removed from the body. The operation of use of other lugs 150, 350, 550, 650, 750, 850, 950 is substantially similar to lug 250 described herein, and thus will be omitted in the interest of brevity.

Figure 12:
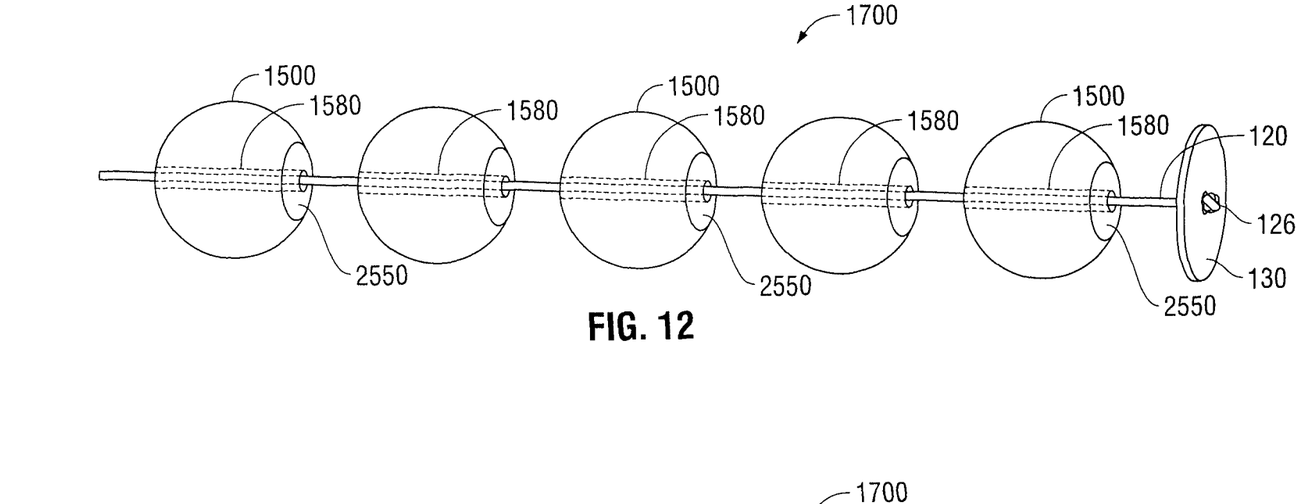
FIG. 12 is a perspective view of a strand of beads in accordance with an embodiment of the present disclosure.
Figure 13:
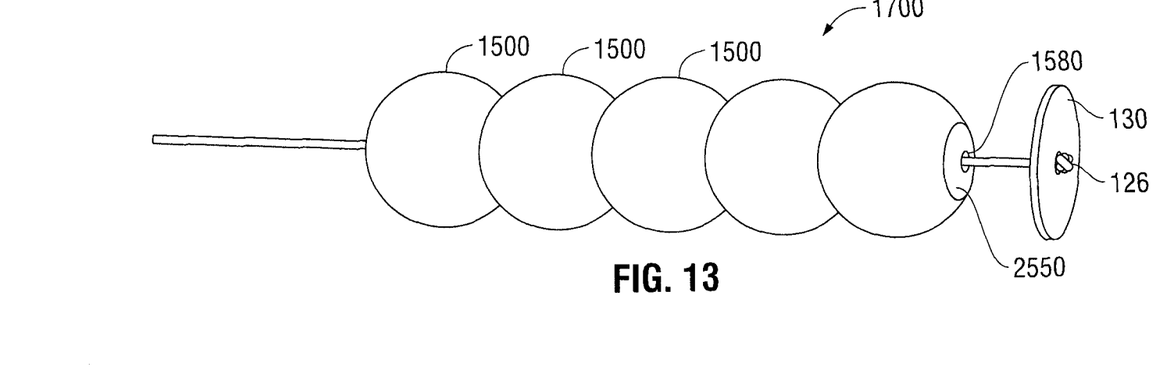
FIG. 13 is a perspective view of the strand of beads of FIG. 12 in a rigid state.
Figure 19A:
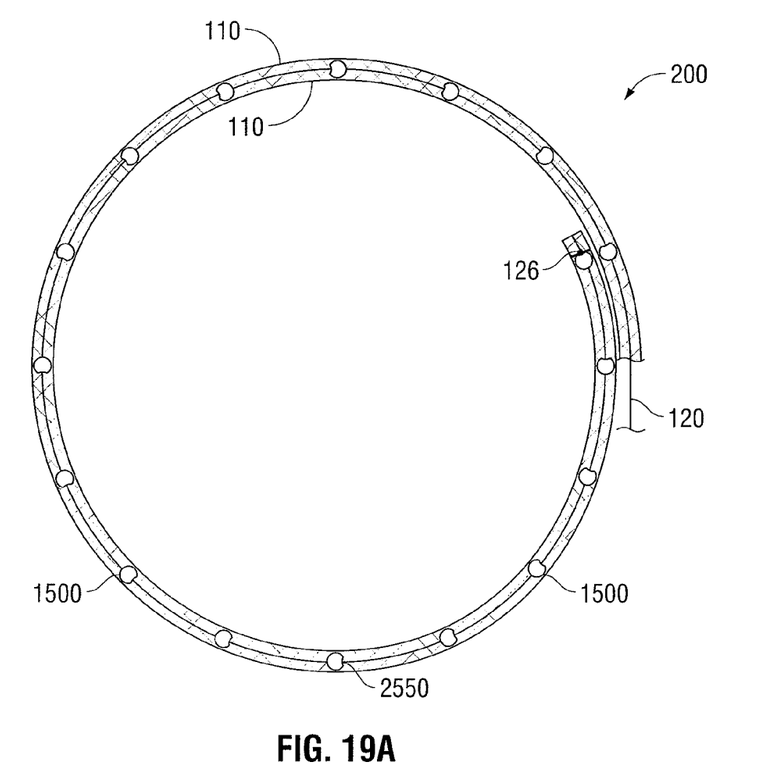
FIG. 19A is a cross-sectional view of a surgical mesh system including a strand of beads of FIG. 12 in a flexible state.
Figure 19B:
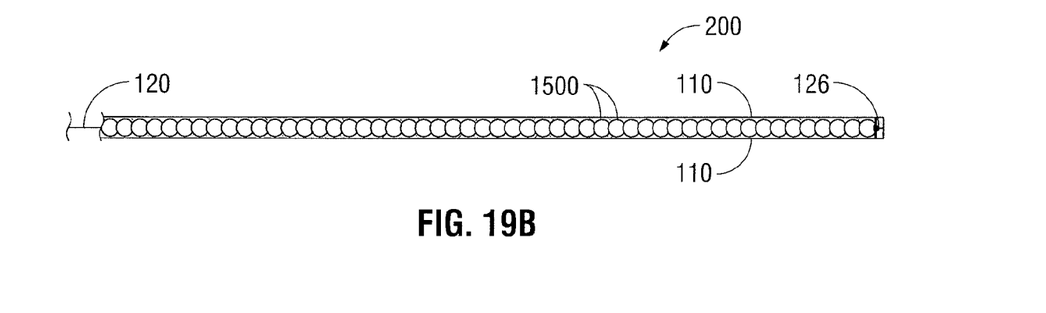
FIG. 19B is a cross-sectional view of the surgical mesh system of FIG. 19A in a rigid state.

With reference now to FIG. 12, another aspect of the present disclosure is shown generally as a bead 1500. Bead 1500 defines a recess portion 2550 and a bore 1580 (shown in phantom). Bore 1580 provides a passage for wire 120 therethrough. The plurality of beads 1500 are interconnected by wire 120 creating a strand 1700 of beads 1500. Strand 1700 may be embedded or woven intermittently in the pair of patches 110 enabling the user to control the shape of a mesh 200 by controlling the tension in wire 120. For example, with little or no tension in wire 120, mesh 200 is in the first flexible state, as shown in FIG. 19A. Upon applying tension to wire 120, beads 1500 nest causing strand 1700 to become rigid, as shown in FIG. 19B. In this manner, mesh 200 expands to the second state without deforming from its intended shape. The flexibility of strand 1700 may be varied by inclusion of more or less wire 120 for a given number of beads 1500. While a single continuous strand 1700 may cover the entire mesh 200, a plurality of strands 1700 may be utilized to accommodate, for example, special mesh shapes. However, in the interest of brevity, a single strand 1700 will be illustrated throughout the application.

Recess portion 2550 is dimensioned and configured to accommodate the curvature of adjacent bead 1500. In particular, recess portion 2550 receives therein a portion of adjacent bead 1500 and further aids alignment of beads 1500 on wire 120. In this manner, when tension is applied to wire 120, beads 1500 may be securely supported on each other. Wire 120 can be a wire, monofilament fiber, multifilament fiber, string or other device that has the capacity to withstand an axial tensile force, but buckles and becomes flexible upon application of an axial compressive force.

As described above, a knot 126 and end stop 130 may be provided at a distal end of wire 120. The strand of beads 1500 may be made to be more or less flexible in the first state by inclusion of more or less wire 120 for a given number of beads 1500. Additional beads 1500 may be added to prevent the mesh from deforming from its intended shape upon application of tension to wire 120. Furthermore, it is contemplated that various shapes and configurations of beads may be used to accommodate special mesh shapes and redirection of the strand, that is, to redirect the tension force in wire 120 to another prescribed direction.

Figure 14:
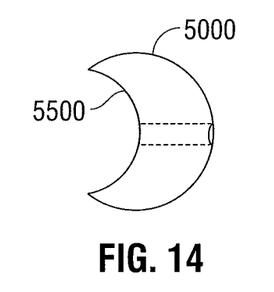
FIG. 14 is a perspective view of a bead in accordance with another embodiment of the present disclosure.
Figure 15:
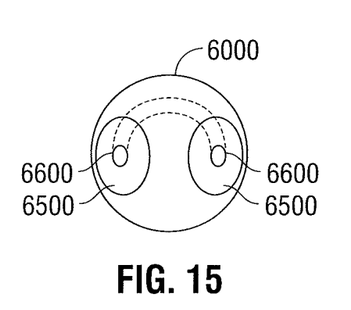
FIG. 15 is a perspective view of a bead in accordance with still another embodiment of the present disclosure.
Figure 16:
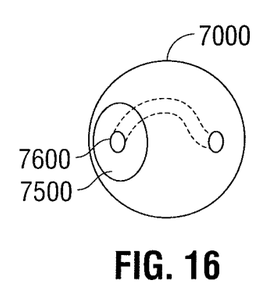
FIG. 16 is a perspective view of a bead in accordance with yet another embodiment of the present disclosure.

With reference to FIG. 14, still another embodiment of a bead is shown as a bead 5000. Bead 5000 defines recess portion 5500 deeper than that of beads 1500. Bead 5000 may be placed between beads 1500, for example, in order to better secure beads 1500 against each other when strand 1700 is in the rigid second state. It is contemplated that in order to facilitate redirection of strand 1700 to another prescribed direction, beads 6000, 7000 may be used, as shown in FIGS. 15 and 16. Bead 6000 includes a pair of recess portions 6500 in communication with a bore 6600 for passage of wire 120 therethrough. The proximity of the pair of recessed portions 6500 may be tailored to accommodate desired shape of the mesh, for example. Bead 7000 includes a single recessed portion 7500 in communication with bore 7600. However, in contrast to bore 1580 of bead 1500, bore 7600 includes a bend portion to facilitate redirection of the strand to another pre-scribed direction. Again, the degree of bend may be tailored to accommodate the desired shape of the mesh, for example. It is envisioned that beads 5000, 6000, 7000 may be used in combination with bead 1500.

Figure 17:
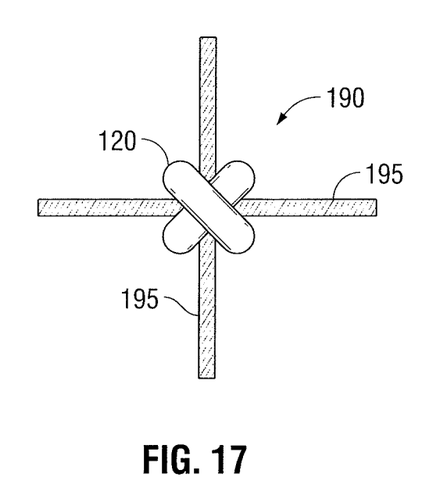
FIG. 17 is a top view of an end stop in accordance with an embodiment of the present disclosure.

In accordance with still another aspect of the present disclosure, an end stop 190 is illustrated in FIG. 17. End stop 190 may include a pair of crossbars 195 substantially orthogonal to each other. A knot may be formed at the intersection of crossbars 195. In this manner, end stop 190 may reduce concentration of the tensile force applied to mesh 100, 200 when placing mesh 100, 200 in the second state.

It is further contemplated that the surgical mesh may be formed of shape memory polymeric materials which are capable of adopting a shape in vivo suitable for adhering tissue or affixing a surgical device to tissue. Shape memory polymeric materials utilized to form a surgical mesh of the present disclosure possess a permanent shape and a temporary shape. In embodiments, the temporary shape is of a configuration which enhances the ability for the surgeon to introduce a surgical mesh into a patient's body. The permanent shape, which is assumed in vivo upon application of energy, such as heat or light, is of a configuration which enhances the retention of the surgical mesh in tissue and/or adhesion of a surgical device to tissue.

Shape memory polymers are a class of polymers that, when formed into an object such as a surgical mesh, can be temporarily deformed by mechanical force and then caused to revert back to an original shape when stimulated by energy. Shape memory polymers exhibit shape memory properties by virtue of at least two phase separated microdomains in their microstructure. The first domain is composed of hard, covalently cross-linked or otherwise chain motion-limiting structures, which act as anchors to retain the object's original shape. The second domain is a switchable soft structure, which can be deformed and then fixed to obtain a secondary or temporary shape.

In addition, the mesh may utilize biodegradable polymers. Suitable biodegradable polymers include, but are not limited to, aliphatic polyesters; polyamides; polyamines; polyalkylene oxalates; poly(anhydrides); polyamidoesters; copoly(ether-esters); poly(carbonates) including tyrosine derived carbonates; poly(hydroxyalkanoates) such as poly(hydroxybutyric acid), poly(hydroxyvaleric acid), and poly(hydroxybutyrate); polyimide carbonates; poly(imino carbonates) such as poly (bisphenol A-iminocarbonate and the like); polyorthoesters; polyoxaesters including those containing amine groups; polyphosphazenes; poly (propylene fumarates); polyurethanes; polymer drugs such as polydiflunisol, polyaspirin, and protein therapeutics; biologically modified (e.g., protein, peptide) bioabsorbable polymers; and copolymers, block copolymers, random copolymers, homopolymers, blends, and combinations thereof.

Suitable non-degradable materials include, but are not limited to, polyolefins such as polyethylene (including ultra high molecular weight polyethylene) and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins such as fluoroethylenes, fluoropropylenes, fluoroPEGSs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polytetramethylene ether glycol; polybutesters, including copolymers of butylene terephthalate and polytetramethylene ether glycol; 1,4-butanediol; polyurethanes; acrylic polymers; methacrylics; vinyl halide polymers and copolymers such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; copolymers of vinyl monomers with each other and olefins such as ethylene-methyl methacrylate copolymers; acrylonitrile-styrene copolymers; ABS resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof. Additionally, non-biodegradable polymers and monomers may be combined with each other.

The mesh described herein includes advantages of simple design and ease of use, as well as immediate reversibility from rigid to supple. The stiffness of the strand may be directly proportional to how much tension is applied to the wire. During deployment, the strand can be made as flexible as the wire for pushing through a trocar and then made to become rigid. Once the mesh has been fixed in place, tension can be removed from the wire and the mesh may be returned to the flexible state to reduce patient discomfort. This device decreases the difficulty and time associated with introducing surgical mesh into the abdominal cavity as well as deploying and orienting the mesh for fixation.

It will be understood that various modifications may be made to the embodiments disclosed herein. Therefore, the above description should not be construed as limiting, but merely exemplifications of embodiments. Those skilled in the art will envision other modification within the scope and spirit of the claims appended thereto.

What is claimed is:

1. A surgical mesh comprising:
   a patch including a first layer and a second layer;
   a plurality of nesting lugs interposed between the first and second layers; and
   a wire interconnecting the plurality of nesting lugs, wherein the plurality of nesting lugs is associated with the patch such that the surgical mesh is movable between a flexible state when there is no tension in the wire and a substantially rigid state when tension is applied to the wire, the plurality of nesting lugs defining at least one contiguous planar surface in the substantially rigid state, each lug including a body portion and a neck portion extending from the body portion, the body portion defining a through hole dimensioned to receive at least a portion of the neck portion of an adjacent lug, wherein the through hole and the neck portion of the adjacent lug are configured to inhibit relative rotation when the neck portion of the adjacent lug is disposed in the through hole.

2. The surgical mesh according to claim 1, wherein the body portion further defines a recess dimensioned to at least partially receive the neck portion of the adjacent lug.

3. The surgical mesh according to claim 2, wherein the recess and the through hole receive the neck portion of the adjacent lug when the surgical mesh is in the substantially rigid state.

4. The surgical mesh according to claim 2, wherein a side of the body portion of each of the plurality of lugs abuts an opposing side of the body portion of an adjacent lug when the plurality of nesting lugs are in the substantially rigid state, whereby the plurality of lugs defines at least one flat surface.

5. The surgical mesh according to claim 2, wherein the neck portion is substantially orthogonal to the body portion.

6. The surgical mesh according to claim 2, wherein the recess is oriented substantially orthogonal to the body portion.

7. The surgical mesh according to claim 1, wherein the neck portion defines a bore configured to receive the wire therethrough, the bore being in communication with the through hole.

8. The surgical mesh according to claim 7, wherein the bore has a diameter smaller than that of at least a section of the wire.

9. The surgical mesh according to claim 1, further comprising an end stop disposed adjacent a distal end of the wire.

10. The surgical mesh according to claim 9, wherein the distal end of the wire includes a knot.

11. The surgical mesh according to claim 1, wherein the plurality of lugs is biodegradable and bioabsorbable.

12. The surgical mesh according to claim 1, wherein the patch defines a planar surface substantially parallel to the at least one contiguous planar surface.

13. The surgical mesh according to claim 1, wherein the through hole is configured to slidably receive the neck portion of the adjacent lug therein.

14. The surgical mesh according to claim 1, wherein the through hole and the neck portion of the adjacent lug have square-shaped cross-sections.

15. The surgical mesh according to claim 1, wherein engagement of the neck portion of the adjacent lug and the through hole inhibits relative rotation therebetween.

* * * * *